(12) United States Patent  
Chen et al.

(10) Patent No.: US 12,648,973 B2  
(45) Date of Patent: Jun. 9, 2026

(54) ACTIVE SUBSTANCE OF *Lactobacillus plantarum* GKM3, A COMPOSITION COMPRISING THEREOF AND ITS USE FOR PROMOTING LONGEVITY

(71) Applicant: GRAPE KING BIO LTD., Taoyuan City (TW)

(72) Inventors: Chin-Chu Chen, Taoyuan City (TW); Yen-Lien Chen, Taoyuan City (TW); Shin-Wei Lin, Taoyuan City (TW); Yen-Po Chen, Taoyuan City (TW); Ci-Sian Wang, Taoyuan City (TW); Yu-Hsin Hou, Taoyuan City (TW); Yang-Tzu Shih, Taoyuan City (TW); Ching-Wen Lin, Taoyuan City (TW); Ya-Jyun Chen, Taoyuan City (TW); Jia-Lin Jiang, Taoyuan City (TW)

(73) Assignee: GRAPE KING BIO LTD., Taoyuan City (TW)

( * ) Notice: Subject to any disclaimer, the term of this patent is extended or adjusted under 35 U.S.C. 154(b) by 686 days.

(21) Appl. No.: 17/583,859

(22) Filed: Jan. 25, 2022

(65) Prior Publication Data

US 2022/0143114 A1 May 12, 2022

Related U.S. Application Data

(62) Division of application No. 16/541,407, filed on Aug. 15, 2019, now abandoned.

(30) Foreign Application Priority Data

Aug. 16, 2018 (TW) .................................. 107128658

(51) Int. Cl.
| | |
|---|---|
| *A61K 35/747* | (2015.01) |
| *A23L 33/135* | (2016.01) |
| *A61K 9/19* | (2006.01) |
| *C12N 1/205* | (2026.01) |
| *A61K 35/00* | (2006.01) |
| *C12R 1/25* | (2006.01) |

(52) U.S. Cl.  
CPC .......... *A61K 35/747* (2013.01); *A23L 33/135* (2016.08); *A61K 9/19* (2013.01); *C12N 1/205* (2021.05); *A23V 2002/00* (2013.01); *A23V 2400/169* (2023.08); *A61K 2035/115* (2013.01); *C12R 2001/25* (2021.05)

(58) Field of Classification Search  
CPC .. A61K 35/747; A61K 2035/115; A61K 9/19; A23V 2400/169; A23V 2002/00; C12R 2001/25; A61P 25/00; A61P 21/00; A61P 25/28; A23L 33/135  
See application file for complete search history.

(56) References Cited

U.S. PATENT DOCUMENTS

| | | | | |
|---|---|---|---|---|
| 9,096,874 B2 * | 8/2015 | Shibamoto | ................ | C12P 7/56 |
| 2016/0067289 A1 | 3/2016 | Berggren et al. | | |

FOREIGN PATENT DOCUMENTS

| | | | | | |
|---|---|---|---|---|---|
| CN | 105505814 A | * | 4/2016 | ............... | C12N 1/20 |
| CN | 106399163 A | * | 2/2017 | ............... | C12N 1/20 |

OTHER PUBLICATIONS

Manzoor et al. Significantly enhanced biomass production of a novel bio-therapeutic strain Lactobacillus plantarum (AS-14) by developing low cost media cultivation. Journal of Biological Engineering. 2017;11(17):1-10.*  
Natarajan et al. Evaluation and optimization of food-grade tannin acyl hydrolase production by a probiotic Lactobacillus plantarum strain in submerged and solid state fermentation. Food and Bioproducts Processing. 2012;90:780-792.*  
Nualkaekul et al. Survival of freeze dried Lactobacillus plantarum in instant fruit powders and reconstituted fruit juices. Food Research Internationsl. 2012;48:627-633.*  
Wu et al. A persistent level of Cisd2 extends healthy lifespan and delays aging in mice. Hum Mol Genet. 2012;21(18):3956-68.*  
Grosicki et al. Gut Microbiota Contribute to Age-Related Changes in Skeletal Muscle Size, Composition, and Function: Biological Basis for a Gut-Muscle Axis. Calcif Tissue Int. 2018;102(4):433-442.*  
Pearson, "Supplement Delivery Methods: What's Best?" education. seekinghealth.com. 2017; pp. 1-4.

* cited by examiner

*Primary Examiner* — Lynn Y Fan  
(74) *Attorney, Agent, or Firm* — Birch, Stewart, Kolasch & Birch, LLP

(57) ABSTRACT

The present invention provides an active substance of Lactic Acid Bacteria, a composition comprising thereof and its use for promoting longevity, especially for increasing Cisd2 gene expression, reducing mitochondrial damage and delaying aging conditions such as nerve degeneration and sarcopenia.

12 Claims, 6 Drawing Sheets

Specification includes a Sequence Listing.

3-month old female and male SAMP8 mice (10 mice per group)

↓

Ambient temperature 25±2°C, humidity 65±5%

Light/dark cycle: 19:00-07:00 (light), 07:00-19:00 (dark)

Tube-feeding samples once per day

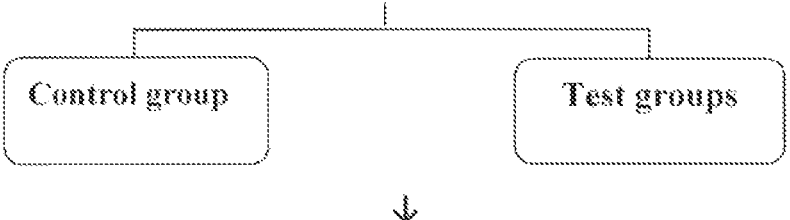

Control group

Test groups

↓

Recording of mice's food & water intake and weight during the experiment

↓

Week 12: aging score measurement

Single-trial passive avoidance test

↓

Week 13: Forearm grip strength test and active shuttle avoidance test

↓

Sacrifice of animals

Fig.4

ACTIVE SUBSTANCE OF *Lactobacillus plantarum* GKM3, A COMPOSITION COMPRISING THEREOF AND ITS USE FOR PROMOTING LONGEVITY

CROSS-REFERENCE TO RELATED APPLICATIONS

This application is a Divisional of U.S. patent application Ser. No. 16/541,407, filed Aug. 15, 2019, which claims priority under 35 U.S.C. § 119 to Taiwanese Patent Application No. 107128658 filed on Aug. 16, 2018, the disclosures of which are hereby incorporated by reference in their entireties.

BACKGROUND

Technical Field

The present invention relates to an active substance of *Lactobacillus plantarum*, a composition comprising thereof and its use for promoting longevity. More specifically, the present invention relates to a composition comprising the active substance, the method for manufacturing the active substance of *Lactobacillus plantarum* GKM3, and the application of GKM3 to increase Cisd2 gene expression, reduce mitochondrial damage and delay aging conditions such as nerve degeneration and sarcopenia when administered to a subject.

Description of Related Art

Longevity Genes

Scientists have long desired to unravel the mystery of longevity. As it has been postulated that the better adjustment to environmental stresses can result in a longer lifespan, the scientists began to search for a group of longevity-affecting genes that relates to environmental stresses (such as extreme weather like scorching heat, or extreme hunger due to lack of food and water). These genes, regardless of the age of the individuals to which they belong, may be able and continue to protect individuals and restore their activity in a natural way, so as to fortify them and help them survive through crises they face. Such genes, also called "longevity genes," may therefore help to improve health and prolong the longevity of individuals significantly as long as they remain active for a long period.

Another group of scientists chose to perform genetic testing on centenarians. They have found that expression levels of certain genes in centenarians are significantly stronger when compared to those in people with average longevity. Therefore, it was postulated that these genes may play a role in determining lifespan.

Cisd2 Gene

Cisd2 gene is a highly evolutionarily conserved gene that can be found in a variety of species, including lower invertebrates, vertebrates and higher mammals. In this respect, Cisd2 gene seems to play a key role in controlling important biological functions. The proteins of Cisd2 gene are expressed on the mitochondrial outer membrane, and a lack of Cisd2 gene in the mitochondria typically leads to mitochondrial damage that undermines the mitochondrial structure and functions and in turn leads to aging. Research on Cisd2 gene knockout mice has shown that they are not only significantly smaller than the control group but also their average life expectancy is barely half of that of the control group. Additionally, Cisd2-knockout mice start to exhibit nerve degeneration and sarcopenia around week 3 (equal to 10 to 12 human years), significant weight loss around week 4 (equal to around 15 human years), protruding eyeballs with white and cloudy spots and osteoporosis around week 8 (equal to around 18-20 human years), and hunchback, blindness, and loose skin around week 12 to 48 (equal to around 30-45 human years). It was further observed that Cisd2 gene expression in normal mice decreases as age increases: the expression drops to 60% around month 14 (equal to around 60 human years) and drops to 30% around month 28 (equal to around 90 human years), when compared mice at young age. Based on past studies and observations listed above, it is confirmed that Cisd2 gene is indispensable for maintaining a normal life expectancy, and is highly associated with aging.

*Lactobacillus* spp.

*Lactobacillus* spp. exist in general environmental conditions and is able to ferment carbohydrates into lactic acid, thereby are often used for manufacturing fermented foods. In the early 1900s, *Lactobacillus* spp. was discovered to bring multiple health benefits such as improving digestion and gut health. Thus, it is recommended to consume *Lactobacillus* spp. for boosting digestive functions and bowel movements. It was further discovered in other studies that lactic acid bacteria can dissolve carbohydrates (such as lactose, glucose, sucrose and fructose) and produce lactic acid and acetic acid, which in turn promotes gut acidification to prevent bad bacteria from proliferating, and allow gut flora to keep a healthy balance.

*Lactobacillus* spp. bacteria, whether of different species or of the same species but different strains, may have distinct characteristics and effects on the human body. For example, it has been found that *Lactobacillus plantarum* may be beneficial to human health. In particular, *L. plantarum* PH04 may lower blood cholesterol; *L. plantarum* 299V may reduce colitis symptoms in IL-10-deficient mice; *L. plantarum* 10hk2 may increase levels of pro-inflammatory mediators, such as interleukin-1β (IL-1β), IL-6 and TNF-α, as well as increase levels of anti-inflammatory mediator IL-10 to counteract inflammation; and *L. plantarum* K21 may lower blood cholesterol and triglyceride, as well as counteract inflammation.

*Bifidobacterium*

*Bifidobacterium* is a genus of gram-positive, nonmotile, rod-shaped and often branched anaerobic bacteria. They are ubiquitous inhabitants of the gastrointestinal tract, vagina and mouth of human and animals. In 1899, they were first isolated from feces of healthy infants, and it was later discovered that certain *Bifidobacterium* strains can be used as probiotics to be added in foods, medicine and feeds.

However, the effects of lactic acid bacteria on longevity have never been mentioned in related studies. Nor have there been experiments which attempt to demonstrate how lactic acid bacteria determine an individual's longevity by altering the physiological conditions thereof through Cisd2 gene expression.

SUMMARY

One object of the present invention is to provide a longevity-promoting composition comprising a *Lactobacil-*

*lus plantarum*, wherein the *Lactobacillus plantarum* is deposited (No. BCRC14565) at China General Microbiological Culture Collection Center (CGMCC) on Aug. 25, 2017 (Institute of Microbiology, Chinese Academy of Sciences, Datun Road, Chaoyang District, Beijing 100101, China).

Another object of the present invention is to provide a longevity-promoting composition comprising an active substance of *Lactobacillus plantarum* of an effective amount, wherein the *Lactobacillus plantarum* is deposited (No.14565) at China General Microbiological Culture Collection Center (CGMCC) on Aug. 25, 2017 (Institute of Microbiology, Chinese Academy of Sciences, Datun Road, Chaoyang District, Beijing 100101, China).

Preferably, the active substance is prepared by the following method:

(a) Streaking bifidobacterial strains onto a solid-state media to produce single colonies; and (b) Inoculating a single colony of lactic acid bacteria cultured at step (a) to a liquid culture for liquid-state culture.

Preferably, the method further comprises the following steps:

(c) Centrifuging the liquid culture containing lactic acid bacteria colony that was cultured at step (b) to obtain a bacterial pellet; and (d) Freeze-dry the bacterial pellet obtained at step (c).

Preferably, step (b) is carried out at 30 to 50° C., in nitrogen or carbon dioxide of 0 to 1 VVM, shake at 10 to 100 rpm, and/or incubate for 16 to 24 hours.

Preferably, the temperature for the freeze-drying at step (d) is −196 to −40° C.

Preferably, the composition includes an additive selected from the group consisting of an excipient, preservative, diluent, filler, absorption enhancer, sweetener and a combination thereof.

Preferably, the composition is a drug, feed, drink, nutritional supplement, dairy product or health food.

Preferably, the composition takes the form of a powder, tablet, granule, suppository, microcapsule, ampoule/ampule, liquid spray or suppository form.

Yet another object of the present invention is to provide a method for manufacturing a composition for promoting longevity.

Preferably, in terms of the method for promoting longevity, a subject having been administered the active substance exhibits increased Cisd2 gene expression compared to a subject that has not been administered the active substance.

Preferably, in terms of the method for promoting longevity, a subject having been administered the active substance exhibits reduced and delayed mitochondrial damage compared to a subject that has not been administered the active substance.

Preferably, in terms of the method for promoting longevity, a subject having been administered the active substance exhibits delayed aging conditions of nerve degeneration, sarcopenia or a combination thereof, compared to a subject that has not been administered the active substance.

BRIEF DESCRIPTION OF THE DRAWINGS

FIG. 4 shows the procedure for the animal experiments.

DETAILED DESCRIPTION

Source of Lactic Acid Bacteria

Figure 1:
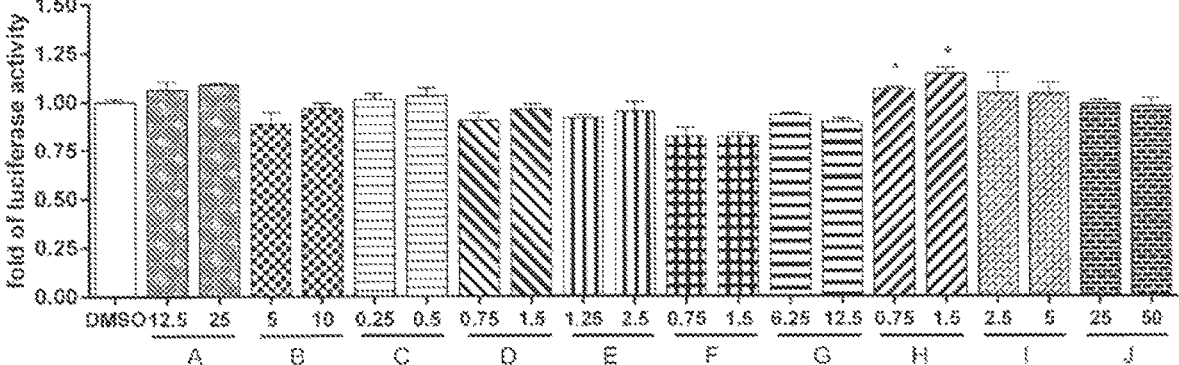
FIG. 1 shows the relative expression levels of Cisd2 gene promoter-controlled fluorescence intensity in HEK293 cells after treating with different lactic acid bacteria (number A to J) active substances at different doses.

The lactic acid bacteria used in the present invention include *Lactobacillus plantarum* and *Bifidobacterium*. In a preferred embodiment, the lactic acid bacteria of the present invention are purchased from the Bioresource Collection and Research Center at Taiwan Food Industry Research and Development Institute. In a preferred embodiment, the lactic acid bacteria used in the following experiments are numbered A to J. The strain and deposit number of each numbered bacteria are shown in Table 1 below. Processes of collection, isolation and purification, as well as results of genetic analysis and assay of bacteria A to H are described in Taiwan patent application No. 106137773 and No. 106136134.

TABLE 1

| Numbers, strains and deposit numbers of lactic acid bacteria | | |
| --- | --- | --- |
| No. | Strain | Deposit number |
| A | *Lactobacillus paracasei* GKS6 | BCRC-910788 |
| | | CGMCC-14566 |
| B | *Lactobacillus johnsonii* | BCRC-19194 |
| C | *Lactobacillus brevis* | BCRC-12187 |
| D | *Lactobacillus plantarum* | BCRC-80061 |
| E | *Lactobacillus plantarum* | BCRC-80581 |
| F | *Lactobacillus plantarum* | BCRC-80577 |
| G | *Lactobacillus plantarum* | BCRC-80578 |
| H | *Lactobacillus plantarum* GKM3 | BCRC-910787 |
| | | CGMCC-14565 |
| I | *Bifidobacterium lactis* GKK2 | BCRC-910826 |
| | | CGMCC-15205 |
| J | *Bifidobacterium lactis* | BCRC-17394 |

Culture of Lactic Acid Bacteria 10 lactic acid bacteria (A to J) listed above were streaked onto a solid-state medium to produce a single colony. In a preferred embodiment, the solid-state medium is MRS agar. Once fully grown, a single colony of lactic acid bacteria is inoculated into a flask containing a liquid medium for liquid culture. In a preferred embodiment, the lactic acid bacteria are cultured in a liquid medium at 35-50° C., in nitrogen or carbon dioxide of 0 to 1 VVM, and rotate at 10 to 100 rpm. In a preferred embodiment, the bacteria are cultured for 16 to 24 hours, more preferably for 18 hours. In a preferred embodiment, the liquid medium is MRS liquid medium. In a preferred embodiment, the ingredients of the liquid medium are shown in Table 2 below.

TABLE 2

| Ingredients of the liquid medium | |
| --- | --- |
| Ingredient | Percentage |
| Glucose | 1~10% |
| Yeast extract | 0.1~5% |
| Peptone | 0.1~5% |
| Trace element | 0.01~2% |
| Cysteine | 0.01~0.1% |
| Tween-80 | 0.05~1% |

Preparation of Freeze-Dried Powder

Once each strain of lactic acid bacteria is fully grown in liquid culture, the lactic acid bacteria are centrifuged to obtain bacterial pellets. In a preferred embodiment, liquid media containing lactic acid bacteria are centrifuged at 1000 to 15000 rpm. The obtained bacterial pellets are mixed with a protecting agent (6-30% skimmed milk powder) and freeze-dried to be preserved at a low temperature. In a preferred embodiment, the freezing temperature is set at −196 to −40° C. In a preferred embodiment, the mixture is freeze-dried for 16 to 72 hours. In a preferred embodiment, the freeze-dried mixture is preserved at −30 to 0° C. The freeze-dried powder of lactic acid bacteria is preserved to be used as an ingredient for the following cell experiments, that is, as one of the embodiments of the lactic acid bacteria active substance claimed by the present application. The embodiments of the lactic acid bacteria active substance claimed by the present application also include the pellet obtained from culturing a single bacterial colony in liquid media as described above.

Cisd2 Luciferase Reporter Gene Assay

A human embryonic kidney cell (HEK293) platform (from Yang-Ming University, Taiwan) that fuses Cisd2 gene promoter, cisd2 gene and luciferase reporter gene, is performed to see whether the active substance of lactic acid bacteria affects Cisd2 gene expression. HEK293 cells carrying luciferase reporter genes ($2 \times 10^5$ cell/mL) are inoculated onto a 6-well plate and incubated in an incubator at 37° C. in 5% $CO_2$ for a day. The preserved freeze-dried powder of the 10 listed above lactic acid bacteria (A-J) is then dissolved in 0.1% DMSO, which serves as a carrier. Various concentrations are prepared from the resulting mixture as shown in Table 3 below, and are added into the HEK293 liquid medium, respectively. In the control group, only the carrier of 0.1% DMSO is added into HEK293 liquid medium while the experimental groups are incubated with different lactic acid bacteria active substance. Both groups are incubated in an incubator at 37° C. in 5% $CO_2$ for 24 hours. The luciferase activity of HEK293 cells is measured and quantified. The above experiment is performed in triplicates. The results are illustrated in FIG. 1.

TABLE 3

| Concentrations of lactic acid bacteria (A to J) freeze-dried powders | | |
| --- | --- | --- |
| No. | Concentration 1 (µg/ml) | Concentration 2 (µg/ml) |
| A | 12.5 | 25 |
| B | 5 | 10 |
| C | 0.25 | 0.5 |
| D | 0.75 | 1.5 |
| E | 1.25 | 2.5 |
| F | 0.75 | 1.5 |
| G | 6.25 | 12.5 |
| H | 0.75 | 1.5 |
| I | 2.5 | 5 |
| J | 25 | 50 |

Endogenous Cisd2 Expression Levels

Figure 2:
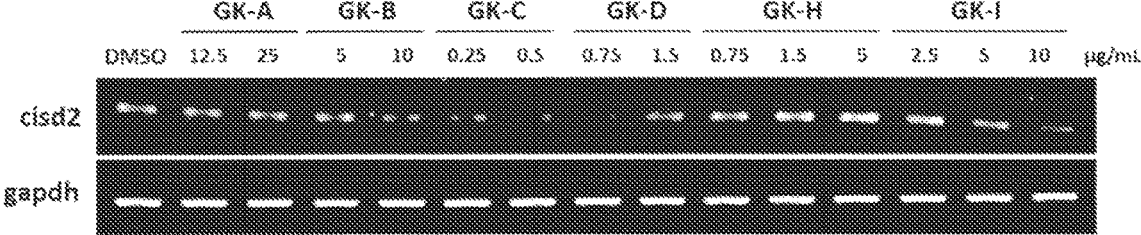
FIG. 2 shows the gel image of the expression levels of endogenous Cisd2 message RNA (mRNA) after treating HEK293 cells with different lactic acid bacteria (number A, B, C, D, H and I) active substances at different doses, respectively.

The activity of endogenous Cisd2 gene is measured to further determine the effects of lactic acid bacteria active substances on Cisd2 expression levels. First, normal HEK293 cells ($2 \times 10^5$ cell/mL) are inoculated onto a 6-well plate and incubated at 37° C. with 5% $CO_2$ in an incubator for a day. Freeze-dried powders of lactic acid bacteria numbered A, B, C, D, H and I are then dissolved in 0.1% DMSO carrier and prepared into mixtures at various concentrations as shown in Table 4 below. Each mixture is then added into a HEK293 cell culture. In the control group, only carrier of 0.1% DMSO is added into the HEK293 cell culture while the experimental groups are incubated with the lactic acid bacteria active substance. Both groups are incubated in an incubator for 24 hours. Cells are then scraped on ice and mRNA is extracted therefrom using the commercially available GeneJET RNA Purification Kit (Thermo). The mRNA extract is adjusted to appropriate concentrations and then reverted into cDNA using the RevertAid H Minus First Strand cDNA Synthesis Kit (Thermo). Finally, endogenous Cisd2 gene expression levels are measured using PCR. The gel image of the results is shown in FIG. 2, and the results in FIG. 2 are statistically analyzed and shown in FIG. 3.

TABLE 4

| Concentrations of lactic acid bacteria (A, B, C, D, H and I) freeze-dried powders | | | |
| --- | --- | --- | --- |
| No. | Concentration 1 (µg/ml) | Concentration 2 (µg/ml) | Concentration 3 (µg/ml) |
| A | 12.5 | 25 | N/A |
| B | 5 | 10 | N/A |
| C | 0.25 | 0.5 | NIA |
| D | 0.75 | 1.5 | N/A |
| H | 0.75 | 1.5 | 5 |
| I | 2.5 | 5 | 10 |

Statistical Method for Analyzing Cisd2 Experimental Data

Data are expressed as mean standard deviation (SD). Differences in activity between the control group and test groups are described as fold changes. Statistical differences between groups are expressed with p values, where *$p<0.05$ is defined as statistically significant, and **$p<0.01$ as statistically highly significant.

Results of Cisd2 Experiments

The results of Cisd2 luciferase reporter gene assay are shown in FIG. 1. Among 10 strains of lactic acid bacteria numbered A to J, HEK293 cells treated with the active substance of bacteria A, C, H and I exhibit greater fluorescence intensity than the control group. These results suggest that the active substance of bacteria A, C, H and I may increase Cisd2 gene expression levels. Regarding the results of bacteria A, the luciferase expression levels are higher than those of the control group when HEK293 cells are stimulated either at a concentration of 12.5 μg/ml or 25 μg/ml. These results indicate that the active substance of bacteria A may increase Cisd2 gene expression levels. Regarding bacteria C, the results are similar to those of bacteria A: the luciferase expression levels are higher than those of the control group when HEK293 cells are stimulated either at a concentration of 0.25 μg/ml or 0.5 μg/ml. Again, such results indicate that the active substance of bacteria C may increase Cisd2 gene expression levels. On the other hand, bacteria H at 1.5 μg/ml exhibits 1.14-fold luciferase expression levels when compared to the control group. Similarly, such results indicate that the active substance of bacteria H may significantly (p<0.05) increase Cisd2 gene expression levels. Regarding bacteria I, the luciferase expression levels are higher than those of the control group when HEK293 cells are stimulated either at a concentration of 2.5 μg/ml or 5 μg/ml, indicating that the active substance of bacteria I may also increase Cisd2 gene expression levels.

Figure 3:
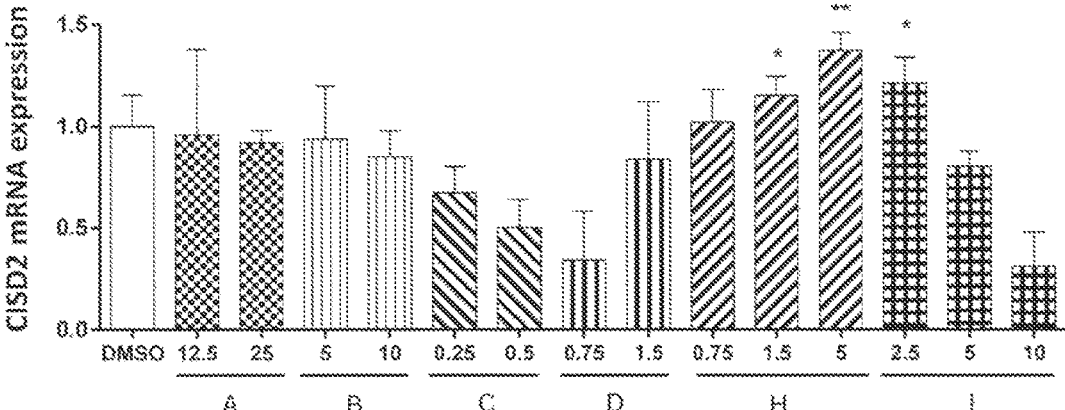
FIG. 3 shows the statistical results of the expression levels of the Cisd2 message RNA (mRNA) in FIG. 2.

The measured results of endogenous Cisd2 gene expression levels are shown in FIGS. 2 and 3. Bacteria A and C did not exhibit higher cisd2 mRNA expression levels when compared to the control group, and bacteria C even exhibits lower mRNA expression levels when compared to the control group. On the other hand, bacteria H and I exhibit higher mRNA expression levels compared to the control group. Both bacteria H, at 1.5 μg/ml and 5 μg/ml, and bacteria I, at 2.5 μg/ml, exhibit statistical significance when compared to the control group, indicating that bacteria H and I significantly raise the mRNA expression levels of Cisd2 gene. Specifically, bacteria H resulted in 1.15-fold mRNA expression levels (p<0.05) at 1.5 μg/ml, and 1.37-fold expression levels (p<0.01) at 5 μg/ml when compared to the control group. The mRNA expressions levels increase when the concentration of lactic acid bacteria active substances increases, showing a concentration-effect relationship. Finally, bacteria I at 2.5 μg/ml resulted in 1.21-fold expressions levels (p<0.05) when compared to the control group.

The above results proved that the active substance of certain lactic acid bacteria (preferably *Lactobacillus paracasei, Lactobacillus plantarum* and *Bifidobacterium*) increased Cisd2 gene expression levels and thereby may extend longevity, which could provide a novel pharmaceutical use of lactic acid bacteria. In view of the above, a composition containing lactic acid bacteria active substance is manufactured for a novel application. Additionally, an effective amount of the composition is determined to be administered to a subject to achieve a desired effect.

In the following experiment, bacteria H (GKM3) is used to determine its effect on delaying aging and promoting longevity. Bacteria I (GKK2) and bacteria A (GKS6) will be claimed in other applications, respectively.

Aging Evaluation in Experimental Animals

The general procedure of the animal experiment in the present invention is shown in FIG. 4. The animals selected to be used in this experiment are senescence-accelerated mice (SAM) developed by Kyoto University (Japan) through a program of selective breeding of AKR/J sibling matings. The SAMP8 mice used in this experiment are characterized by cerebral neuron loss, cerebral atrophy, lipofuscin deposits, cavernous malformations in reticular formation of brainstem and amyloid protein deposits. Other characteristics include rapid aging of other organs and shortened life span, which makes them an ideal experimental animal model for studies related to delayed aging and reproductive functions. These mice were housed in a 30(W)×20(D)×10(H) cm³ transparent plastic cage in a dust-free, automated room with a temperature of 25±2° C. and a relative humidity of 65±5%. Light cycle was controlled by an automatic timer, with a dark period set from 07:00 to 19:00 and a light period set from 19:00 to 07:00.

This experiment was designed in accordance with "Regulations and Evaluative Methods for Health Foods of Aging-Delaying and Health-Promoting Functions." Three-months old male and female SAM-P8 mice were used as experimental animals. The mice were first divided into a control group and two test groups (high- and low-dose groups treated with lactic acid bacteria H), and each group was then divided into female and male groups, resulting in a total of 6 groups with 10 mice per group (60 mice in total). The mice in the control group were tube-fed with ddH₂O samples, while those in the test groups were tube-fed with ddH₂O-dissolved freeze-dried powders of lactic acid bacteria H (GKM3), which were prepared at desired doses, respectively. Groups and the dose used in the respective group are shown in Table 5 below.

TABLE 5

| Group | Sample (Lactic acid bacteria H, GKM3) | Dose |
|---|---|---|
| Control group | ddH₂O | 10 ml/day |
| Low-dose group | Lactic acid bacteria H | 1.02 × 10⁹ cfu/kgBW/day |
| High-dose group | Lactic acid bacteria H | 5.1 × 10⁹ cfu/kgBW/day |

The experiment was carried out over 13 weeks, during which each group was tube-fed with respective samples once a day. Food and water intake of each group were recorded during the experiment. At week 12, the mice were assessed by means of aging score and were given a single-trial passive avoidance test. At week 13, the mice were given an active shuttle avoidance test. After the tests, the mice were subject to $CO_2$ asphyxiation and sacrificed by decapitation (fasted for 8 hours before sacrifice). Blood and organs of the decapitated mice were collected for analysis.

Aging Score

The grading score system was devised in 1981 by Takeda and other scholars for measuring the frailty level of SAM mice. To measure the aging level of the mice used in this experiment, six measure items were selected as follows: hair glossiness, hair coarseness, loss of hair, skin ulcers, periophthalmic lesion, and lordokyphosis of the spine. The aging level of the mice was graded on a scale of 0 to 4. The score obtained for each item was added up and resulted in a final score. Mice with a higher score exhibited a higher aging level.

Forearm Grip Strength Test

Aging may cause degenerated physiological functions or multiple chronic diseases that lead to accelerated muscle disuse atrophy. Typically, people lose 1-2% of their muscles per year after age 30, and dramatically decreases as much as 15% per year after age 60. The loss of muscle biomass is a risk factor that may lead to subsequent negative health events, including disabilities, falling, function degeneration, being bedridden and even death.

Aging-induced skeletal muscle loss may develop sarcopenia, which is also called "skeletal muscle aging" or "senile skeletal wasting." Sarcopenia exhibits three major symptoms: (1) low muscle mass; (2) low muscle strength; and (3) low physical performance. In 2010, European Union Geriatric Medicine Society (EUGMS) developed and published diagnostic criteria and a definition of aging-induced sarcopenia: persons over 65 years of age with a gait speed of less than 1 m/sec, poor grip strength and a muscle mass smaller than a critical value will be diagnosed as having sarcopenia. The data collected from the internal medicine and family medicine division at National Taiwan University Hospital showed that the prevalence of sarcopenia increased from 18% to 64% among middle-aged men, and 9% to 41% among middle-aged women, as their age increased. Clinically, the worsening of sarcopenia and muscle weakness can be delayed by implementing effective interventions and diagnostics to prevent subsequent negative health events from occurring.

In the mice experiment, a Grip Strength Meter (GSM, Cat. No. 47200) was used for measuring the forearm grip strength of SAMP8 mice to determine their muscular strength. The method was carried out by holding the animal by tail and causing it to grasp the pull bar with its forepaws. The animal was then pulled back horizontally on its tail until its grip was released. The force applied at this point was recorded using the GSM for three consecutive times, and the highest value recorded was chosen and analyzed statistically.

Single-Trial Passive Avoidance Test

The effects of lactic acid bacteria on the learning and memory in mice were measured by way of classical conditioning and the animal's preference for darkness. A special box divided into a light chamber and a dark chamber by a central gate was used for this experiment, with the chambers being designed to be connected to each other, and an array of parallel metal rods connected to a power supply being placed on the bottom of the box. At the start of the test, the mice were placed in the light chamber with the gate opened to allow for exploration. The gate was closed as soon as the mice entered the dark chamber, and the mice were then given an electric shock (0.5 µA, 0.5 s) once to be trained for learning. 24, 48 and 72 hours after the end of the training, the mice's memory was measured by recording the latency time in the light chamber. The maximum duration time is set for 180 s. A longer latency time in the light chamber indicated a better learning and memory.

Active Shuttle Avoidance Test

The effects of lactic acid bacteria on the learning and memory in mice were measured by way of classical conditioning and the animal's avoidance from light and sound stimuli. A special box divided into a light chamber and a dark chamber by a central gate was used for this experiment, with the chambers being designed to be connected to each other, and an array of parallel metal rods connected to a power supply being placed on the bottom of the box. All mice were given light and sound stimuli for 10 s (conditioned stimulus, CS), and were further given an electric shock (unconditioned stimulus, UCS) for those showed no avoidance from the CS. However, for those who avoided the CS, the electric shock was not given. The experimental animals were given the above avoidance test with CS/UCS for 4 consecutive days, 4 times per day and 5 rounds each time. This test aims at determining the learning and memory in mice by measuring the times they would exhibit avoidance under such test conditions. A higher active avoidance time indicated a better learning and memory.

Statistical Methods Used in the Animal Experiment

The data collected from this study were analyzed using SPSS statistical software. The results Obtained were expressed as mean±SEM and analyzed by one-way analysis of variance (one-way ANOVA) to test for differences among multiple test groups. Differences between pairs of groups were measured using Duncan's Multiple Range test. $p<0.05$ indicates a statistically significant difference.

Results Obtained from the Animal Experiment

Results Obtained from the aging score test for each group are shown in Tables 6 and 7 below:

TABLE 6

| Aging scores of female mice | | | |
|---|---|---|---|
| Item | Control group | GKM3-low dose | GKM3-high dose |
| Skin | | | |
| Glossiness | 1.00 ± 0.00 [a] | 0.60 ± 0.16 [b] | 0.00 ± 0.00 [c] |
| Coarseness | 0.90 ± 0.10 [a] | 0.10 ± 0.10 [b] | 0.00 ± 0.00 [b] |
| Hair loss | 0.50 ± 0.17 [a] | 0.20 ± 0.13 [b] | 0.00 ± 0.00 [b] |
| Ulcer | 0.00 ± 0.00 | 0.00 ± 0.00 | 0.00 ± 0.00 |
| Eye | | | |
| Periophthalmic lesion | 1.50 ± 0.22 [a] | 0.90 ± 0.10 [b] | 0.60 ± 0.16 [b] |
| Spine | | | |
| Lordokyphosis of the spine | 1.00 ± 0.00 [a] | 0.50 ± 0.17 [b] | 0.40 ± 0.16 [b] |
| Total | 4.90 ± 0.23 [a] | 2.30 ± 0.37 [b] | 1.00 ± 0.26 [c] |

Values were expressed as mean ± S.E.M. and analyzed by one-way ANOVA. (n = 10)
⋅X⋅Same superscript letters indicate no statistically significant differences between groups.

TABLE 7

| Aging scores of male mice | | | |
|---|---|---|---|
| Item | Control group | GKM3-low dose | GKM3-high dose |
| Skin | | | |
| Glossiness | 0.50 ± 0.17 | 0.20 ± 0.13 | 0.20 ± 0.13 |
| Coarseness | 0.80 ± 0.13 | 0.30 ± 0.15 | 0.30 ± 0.15 |
| Hair loss | 0.20 ± 0.13 | 0.00 ± 0.00 | 0.00 ± 0.00 |
| Ulcer | 0.00 ± 0.00 | 0.00 ± 0.00 | 0.00 ± 0.00 |
| Eye | | | |
| Periophthalmic lesion | 0.80 ± 0.13 | 0.40 ± 0.16 | 0.20 ± 0.13 |
| Spine | | | |
| Lordokyphosis of the spine | 0.70 ± 0.15 | 0.40 ± 0.16 | 0.40 ± 0.16 |
| Total | 3.00 ± 0.33 [a] | 1.30 ± 0.26 [b] | 1.10 ± 0.35 [b] |

Values were expressed as mean ± S.E.M. and analyzed by one-way ANOVA. (n = 10)
⋅X⋅Same superscript letters indicate no statistically significant differences between groups.

In view of the aging scores obtained from the test at week 12, both 3-months old female and male SAMP8 mice fed with high- and low-dose lactic acid bacteria H (GKM3) exhibited significantly lower scores than control groups. Female mice, in particular, exhibited a more significant reduction (p<0.05). Higher aging scores (as shown in Tables 6 and 7) indicated higher levels of aging. These results show that feeding SAMP8 mice with lactic acid bacteria H (GKM3) samples may help lower aging scores. Thus, it is clear that lactic acid bacteria H (GKM3) are useful in preventing aging.

Figure 5:
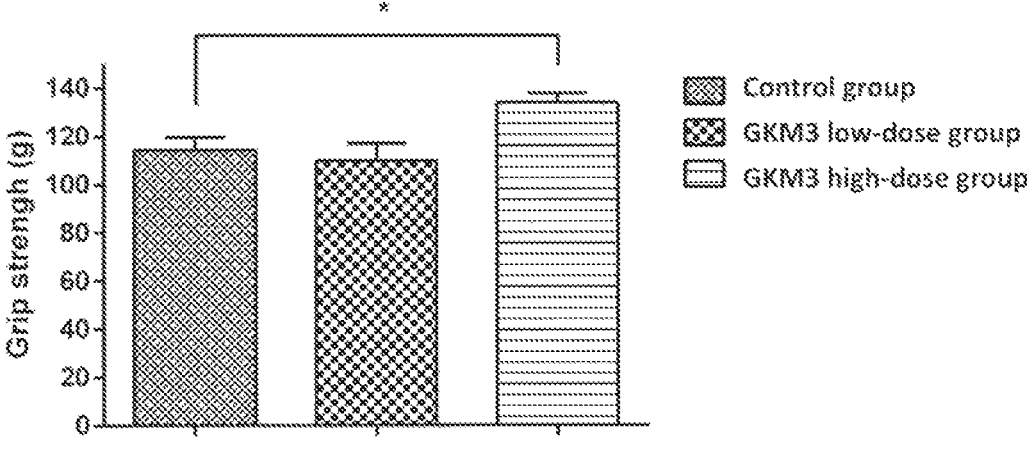
FIG. 5 shows the grip strength exhibited by the male mice during the forearm grip strength test.

The results obtained in male mice groups from the forearm grip strength test are shown in Table 8 and summarized statistically in FIG. 5:

TABLE 8

| Forearm grip strength test in male mice groups | |
| --- | --- |
| Group | Grip strength (g) |
| Control group | 114.4 ± 5.43 |
| GKM3-low dose | 109.98 ± 7.11 |
| GKM3-high dose | 133.98 ± 3.96* |

Values were expressed as mean ± S.E.M. and analyzed by one-way ANOVA. (n = 10)
*Indicates statistically significant differences (p < 0.05) compared to control group.

In view of the grip strength values obtained from the test at week 13, both 3-months old female and male SAMP8 mice fed with high-dose lactic acid bacteria H (GKM3) exhibited significantly higher values (p<0.05) than control groups. Higher grip strength values indicated greater muscle strength. These results show that feeding mice with lactic acid bacteria H (GKM3) samples may help improve muscle strength. Thus, it is clear that lactic acid bacteria H (GKM3) are useful in alleviating aging-induced sarcopenia.

Figure 6:
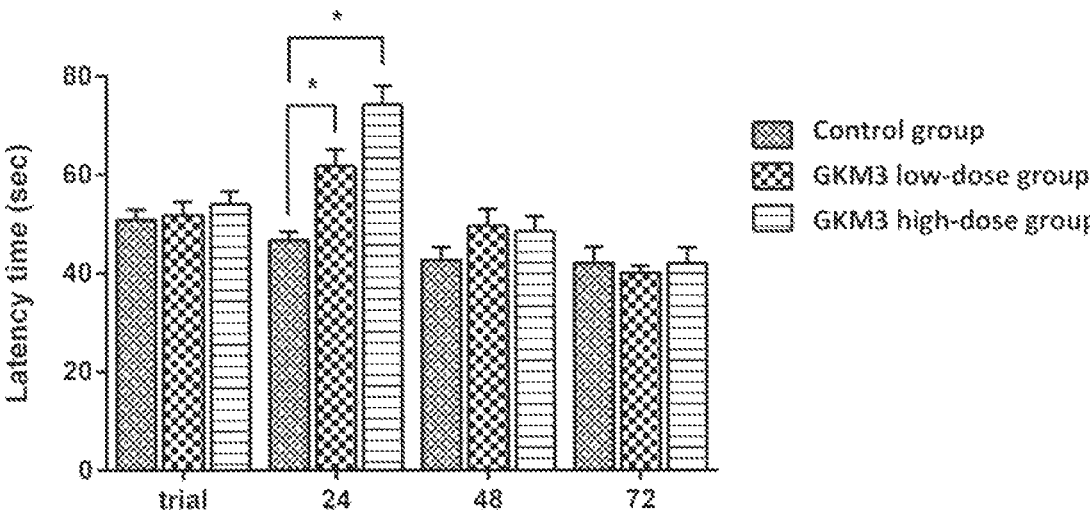
FIG. 6 shows the latency time exhibited by the female mice during the single-trial passive avoidance test.
Figure 7:
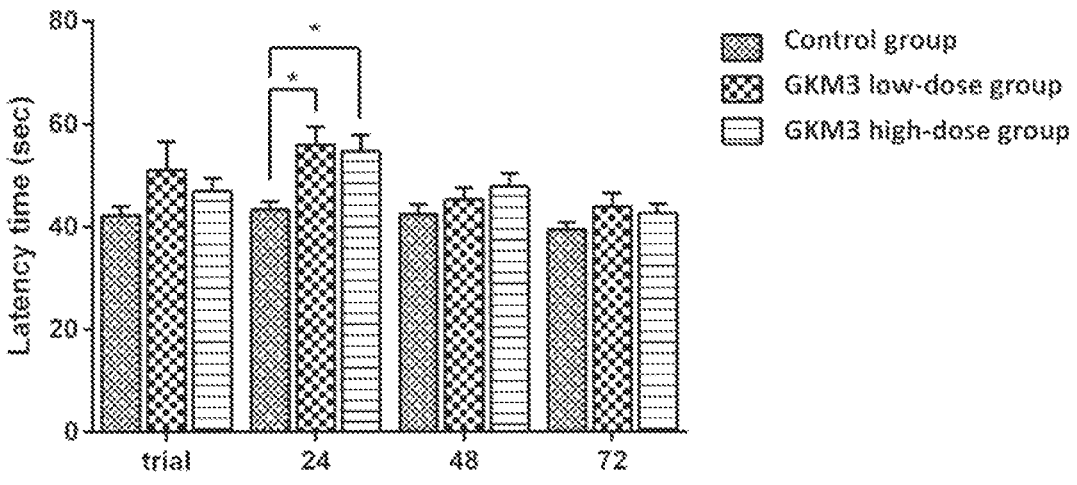
FIG. 7 shows the latency time exhibited by the male mice during the single-trial passive avoidance test.

The results obtained in female mice groups from the single-trial passive avoidance test are shown in Table 9 and summarized statistically in FIG. 6, while the results of single-trial passive avoidance test in male mice groups are shown in Table 10 and summarized statistically in FIG. 7:

TABLE 9

| Single-trial passive avoidance test in female mice groups | | | | |
| --- | --- | --- | --- | --- |
| | | Latency time (sec) | | |
| Group | trial | 24 hr | 48 hr | 72 hr |
| Control group | 50.80 ± 1.99 | 46.60 ± 1.85 | 42.60 ± 2.72 | 41.90 ± 3.31 |
| GKM3-low dose | 51.80 ± 2.67 | 61.70 ± 3.35* | 49.60 ± 3.39 | 40.00 ± 1.31 |
| GKM3-high dose | 53.90 ± 2.65 | 74.10 ± 3.93* | 48.40 ± 3.15 | 41.80 ± 3.28 |

Values were expressed as mean ± S.E.M. and analyzed by one-way ANOVA. (n = 10)
*Indicates statistically significant differences (p < 0.05) compared to control group.

TABLE 10

| Single-trial passive avoidance test in male mice groups | | | | |
| --- | --- | --- | --- | --- |
| | | Latency time (sec) | | |
| Group | trial | 24 hr | 48 hr | 72 hr |
| Control group | 42.20 ± 1.78 | 43.30 ± 1.51 | 42.30 ± 1.93 | 39.40 ± 1.28 |
| GKM3-low dose | 51.10 ± 5.56 | 55.90 ± 3.54* | 45.20 ± 2.30 | 43.80 ± 2.67 |

TABLE 10-continued

| Single-trial passive avoidance test in male mice groups | | | | |
| --- | --- | --- | --- | --- |
| | | Latency time (sec) | | |
| Group | trial | 24 hr | 48 hr | 72 hr |
| GKM3-high dose | 46.90 ± 2.54 | 54.60 ± 3.25* | 47.70 ± 2.45 | 42.60 ± 1.77 |

Values were expressed as mean ± S.E.M. and analyzed by one-way ANOVA. (n = 10)
*Indicates statistically significant differences (p < 0.05) compared to control group.

In view of the latency time obtained from the test at week 13, both 3-months old female and male SAMP8 mice fed with high- and low-dose lactic acid bacteria H (GKM3) exhibited significantly longer latency times than control groups. At 24 hr in particular, mice exhibited a more significant elevation (p<0.05) in latency time. Longer latency time indicated stronger learning and memory. These results show that feeding mice with lactic acid bacteria H (GKM3) samples may help enhance learning and memory in mice. Thus, it is clear that lactic acid bacteria H (GKM3) are useful in preventing aging.

Figure 8:
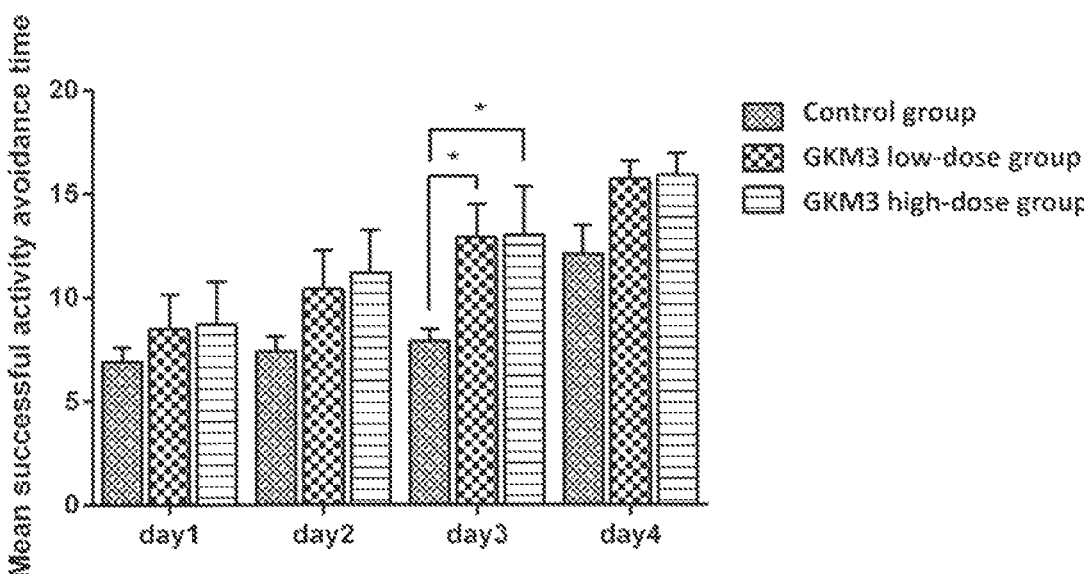
FIG. 8 shows the number of avoidance responses exhibited by the female mice during the active shuttle avoidance test.
Figure 9:
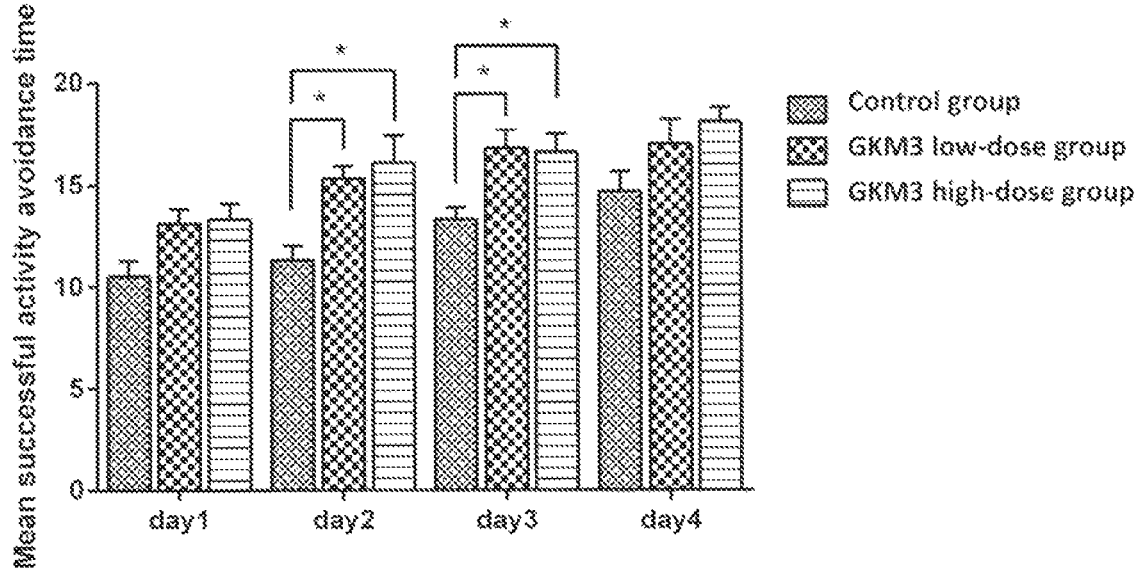
FIG. 9 shows the number of avoidance responses exhibited by the male mice during the active shuttle avoidance test.

The results obtained in female mice groups from the active shuttle avoidance test are shown in Table 11 and summarized statistically in FIG. 8, and the results of the active shuttle avoidance test in male mice groups are shown in Table 12 and summarized statistically in FIG. 9:

TABLE 11

| Active shuttle avoidance test in female mice groups | | | | |
| --- | --- | --- | --- | --- |
| | Mean successful active avoidance responses | | | |
| Group | Day 1 | Day 2 | Day 3 | Day 4 |
| Control group | 6.90 ± 0.69 | 7.40 ± 0.75 | 7.90 ± 0.59 | 12.10 ± 1.36 |
| GKM3-low dose | 8.50 ± 1.65 | 10.40 ± 1.87 | 12.90 ± 1.59* | 15.70 ± 0.87 |
| GKM3-high dose | 8.70 ± 2.07 | 11.20 ± 2.04 | 13.00 ± 2.35* | 15.90 ± 1.05 |

Values were expressed as mean ± S.E.M. and analyzed by one-way ANOVA. (n = 10)
*Indicates statistically significant differences (p < 0.05) compared to control group.

TABLE 12

| Active shuttle avoidance test in male mice groups | | | | |
| --- | --- | --- | --- | --- |
| | Mean successful active avoidance responses | | | |
| Group | Day 1 | Day 2 | Day 3 | Day 4 |
| Control group | 10.50 ± 0.75 | 11.30 ± 0.70 | 13.30 ± 0.58 | 14.70 ± 0.97 |
| GKM3-low dose | 13.10 ± 0.72 | 15.30 ± 0.62* | 16.80 ± 0.89* | 17.00 ± 1.22 |
| GKM3-high dose | 13.30 ± 0.80 | 16.10 ± 1.32* | 16.60 ± 0.88* | 18.10 ± 0.72 |

Values were expressed as mean ± S.E.M. and analyzed by one-way ANOVA. (n = 10)
*Indicates statistically significant differences (p < 0.05) compared to control group.

In view of the avoidance responses obtained from the test at week 14, both 3-months old female and male SAMP8 mice fed with lactic acid bacteria samples exhibited no significant differences with control groups. This is because they were still at learning phase on day 1 and day 2 after feeding. However, female groups on day 3 and male groups on day 2 and 3 exhibited more successful avoidance responses with significant differences (p<0.05) compared to control groups. More successful avoidance responses indicated stronger learning and memory capabilities. These results show that feeding mice with lactic acid bacteria H (GKM3) samples may help enhance learning and memory in mice. Thus, it is clear that lactic acid bacteria H (GKM3) are useful in improving learning and memory that have been undermined by aging-induced nerve degeneration.

To sum up, it can be proved from the above test results that lactic acid bacteria, particularly *Lactobacillus*, preferably lactic acid bacteria H (GKM3), are clearly useful in increasing the expression of Cisd2 gene (the "longevity gene"), improving various aging scores, grip strength, as well as enhancing learning and memory. Hence, the active substance of lactic acid bacteria H (GKM3) is useful in promoting longevity.

The term "effective amount" used herein refers to an amount that is sufficient to produce said preventive and/or therapeutic effects. In in vitro cell culture experiments, the said effective amount is expressed in μg/mL and is based on the total volume of the culture medium used in cell culture. In animal experiments, the said effective amount is expressed as "g/60 kg body weight/day." In addition, the effective amount data obtained from in vitro cell culture experiments may be converted into an effective amount suitable for animals using the following formula:

I. Generally speaking (see Reagan-Shaw et al., 2008), 1 "μg/mL" (based on an effective amount calculated from in vitro cell culture experiments) is equivalent to 1 "mg/kg body weight/day" (based on an effective amount calculated from mice model experiments). An effective dose for humans can be further calculated given the fact that the metabolic rate in mice is six times as high as in humans.

II. Therefore, when the effective amount calculated from in vitro cell culture experiments is 500 μg/mL, the effective amount in mice can be determined as 500 mg/kg body weight/day (i.e. 0.5 g/kg body weight/day). Furthermore, the effective amount in humans can be determined as 5 g/60 kg body weight/day considering the above-mentioned mice-human difference in metabolic rate.

III. Given the test results described in the previous paragraph, the effective amount based on in vitro cell culture experiments is 1.5 μg/mL. As such, it is assumed that the effective amount in mice should be 1.5 mg/kg body weight/day, and the reasonably effective amount in humans should thus be 0.015 g/60 kg body weight/day.

In a preferred embodiment, the effective amount of the lactic acid bacteria active substance contained in the composition is 10 mg/60 kg-1 g/60 kg body weight/day.

The composition further comprises an additive. In a preferred embodiment, the additive can be an excipient, preservative, diluent, filler, absorption enhancer, sweetener or a combination thereof. The excipient can be selected from sodium citrate, calcium carbonate, calcium phosphate, sucrose or a combination thereof. The preservative, such as benzyl alcohol and parabens, can prolong the shelf life of pharmaceutical compositions, The diluent can be selected from water, ethanol, propylene glycol, glycerol or a combination thereof. The filler can be selected from lactose, high molecular weight polyethylene glycol or a combination thereof. The absorption enhancer can be selected from dimethyl sulfoxide (DMSO), laurocapram, propylene glycol, glycerol, polyethylene glycol or a combination thereof. The sweetener can be selected from Acesulfame K, aspartame, saccharin, sucralose, neotame or a combination thereof. In addition to the additives listed above, other ones may be selected according to actual needs provided that the pharmaceutical effects of the lactic acid bacteria active substance are not affected.

The composition can be developed into various products in the pharmaceutical industry. In a preferred embodiment, the composition is a drug, feed, drink, nutritional supplement, dairy product or health food.

The composition can take various forms to meet the subject's needs. In a preferred embodiment, the composition can be in powder, tablet, granule, suppository, microcapsule, ampoule/ampule, liquid spray or suppository form.

The composition of the present invention can be administered to an animal or a human. Provided that the effects of the lactic acid bacteria active substance are not affected, it can be made into any dosage forms and administered via an appropriate route to the animal or human depending on the dosage form.

Preparation of Composition

When the lactic acid bacteria active substance of the present invention is of dietary use, the form of the composition 1 as described below shall be an illustrative example of the lactic acid bacteria active substance.

Composition 1: Freeze-dried powder of the lactic acid bacteria H (GKM3) was used as lactic acid bacteria active substance (20 wt %), and was well-mixed with benzyl alcohol used as a preservative (8 wt %) and glycerol used as a diluent (7 wt %). The resulting mixture was dissolved in pure water (65 wt %) and stored at 4° C. for future use. The notation "wt %" refers to the proportion of the weight of each ingredient relative to the total weight of the composition.

When the lactic acid bacteria, active substance of the present invention is of medical use, the form of the composition 2 as described below shall be an illustrative example of the lactic acid bacteria active substance.

Composition 2: Freeze-dried powder of the lactic acid bacteria H (GKM3) was used as lactic acid bacteria active substance (20 wt %), and was well-mixed with benzyl alcohol used as a preservative (8 wt %), glycerol used as a diluent (7 wt %), and sucrose used as a diluent (10 wt %). The resulting mixture was dissolved in pure water (55 wt %) and stored at 4° C. for future use. The notation "wt %" refers to the proportion of the weight of each ingredient relative to the total weight of the composition.

Deposit number of lactic acid bacteria H (GKM3): CGMCC No. 14565

Deposit number of lactic acid bacteria I (GKK2): CGMCC No. 15205

Deposit number of lactic acid bacteria A (GKS6): CGMCC No. 14566

SEQUENCE LISTING

The patent contains a lengthy sequence listing. A copy of the sequence listing is available in electronic form from the USPTO web site (https://seqdata.uspto.gov/docdetail?docId=US12648973B2). An electronic copy of the sequence listing will also be available from the USPTO upon request and payment of the fee set forth in 37 CFR 1.19(b)(3).

What is claimed is:

1. A method of increasing Cisd2 gene expression in a subject, comprising:

administering an effective amount of a composition to a subject;

wherein the composition comprising an active substance of *Lactobacillus plantarum* of an effective amount, wherein the *Lactobacillus plantarum* No. 14565 is deposited at China General Microbiological Culture Collection Center;

wherein the active substance is prepared by the following method:

(a) streaking the *Lactobacillus plantarum* on a solid-state media to produce single colonies; and (b) inoculating a single colony of the *Lactobacillus plantarum* cultured at step (a) to a liquid culture for liquid-state culture;

(c) centrifuging the liquid culture cultured at step (b) to obtain a bacterial pellet; and (d) freeze-drying the bacterial pellet obtained at step (c);

wherein the active substance is a freeze-dried *Lactobacillus plantarum*.

2. The method of claim 1, wherein step (b) is carried out at 30 to 50° C., in nitrogen or carbon dioxide of 0 to 1 VVM, rotate at 10 to 100 rpm, or incubate for 16 to 24 hours.

3. The method of claim 1, wherein a temperature for the freeze-drying at step (d) is −196 to −40° C.

4. The method of claim 1, the composition comprising an additive selected from the group consisting of an excipient, preservative, diluent, filler, absorption enhancer, sweetener and a combination thereof.

5. The method of claim 1, the composition being a drug, feed, drink, nutritional supplement, dairy product or health food.

6. The method of claim 1, the composition taking the form of a powder, tablet, granule, suppository, microcapsule, ampoule/ampule, liquid spray or suppository form.

7. The method of claim 1, wherein, after the administering step, the subject exhibits reduced and delayed mitochondrial damage compared to a subject that has not been administered the active substance.

8. The method of claim 1, wherein, after the administering step, the subject exhibits delayed aging conditions of nerve degeneration, sarcopenia or a combination thereof, compared to a subject that has not been administered the active substance.

9. A method of delaying nerve degeneration and sarcopenia in a subject, comprising:

administering an effective amount of a composition to a subject;

wherein the composition comprising an active substance of *Lactobacillus plantarum* of an effective amount, wherein the *Lactobacillus plantarum* No. 14565 is deposited at China General Microbiological Culture Collection Center;

wherein the active substance is prepared by the following method:

(a) streaking the *Lactobacillus plantarum* on a solid-state media to produce single colonies; and (b) inoculating a single colony of the *Lactobacillus plantarum* cultured at step (a) to a liquid culture for liquid-state culture;

(c) centrifuging the liquid culture cultured at step (b) to obtain a bacterial pellet; and (d) freeze-drying the bacterial pellet obtained at step (c);

wherein the active substance is a freeze-*dried Lactobacillus plantarum*.

10. The method of claim 9, wherein step (b) is carried out at 30 to 50° C., in nitrogen or carbon dioxide of 0 to 1 VVM, rotate at 10 to 100 rpm, or incubate for 16 to 24 hours.

11. The method of claim 9, wherein, after the administering step, the subject exhibits reduced and delayed mitochondrial damage compared to a subject that has not been administered the active substance.

12. The method of claim 9, wherein, after the administering step, the subject exhibits delayed aging conditions of nerve degeneration, sarcopenia or a combination thereof, compared to a subject that has not been administered the active substance.

* * * * *